United States Patent [19]
Faingold

[11] Patent Number: 5,981,453
[45] Date of Patent: Nov. 9, 1999

[54] PROCESS FOR THE PREPARATION OF TENSIDE MIXTURES

[75] Inventor: Samuil Faingold, Lenesea, Kans.

[73] Assignee: Oy Faintend Ltd., Salo, Finland

[21] Appl. No.: 08/648,050

[22] PCT Filed: Nov. 17, 1993

[86] PCT No.: PCT/FI93/00487

§ 371 Date: May 2, 1997

§ 102(e) Date: May 2, 1997

[87] PCT Pub. No.: WO95/14071

PCT Pub. Date: May 26, 1995

[51] Int. Cl.$^6$ .............................. A61K 7/48; A61K 7/50
[52] U.S. Cl. ........................... 510/159; 554/68; 554/187; 554/188; 554/96; 554/97; 554/98; 554/99; 554/190
[58] Field of Search ............................ 554/68, 187, 188, 554/96, 97, 98, 99, 190; 510/159

[56] References Cited

U.S. PATENT DOCUMENTS

| 3,804,819 | 4/1974 | Wengrow et al. | 260/97.6 |
| 4,753,747 | 6/1988 | Clark et al. | 252/90 |
| 5,308,372 | 5/1994 | Daniels | 71/25 |

*Primary Examiner*—Yogendra Gupta
*Assistant Examiner*—Gregory E. Webb

[57] ABSTRACT

Process for the preparation of a tenside mixture, wherein a starting mixture containing an alkali metal salt of an alkyl sulfonic acid is treated with a concentrated sulfuric acid solution in an amount in excess of the amount needed for converting the salts to organic acids with stirring and cooling such that the temperature of the mixture does not exceed about 35° C., the reaction mixture being allowed to separate into two layers, one layer containing the organic acids, wherein the one layer containing the organic acids is separated and neutralized with di- or triethanolamine in order to prepare di- or triethanolamine salts of the said acids.

11 Claims, No Drawings

PROCESS FOR THE PREPARATION OF TENSIDE MIXTURES

The object of the present invention is a novel process for the preparation of tenside mixtures.

As is known, cleansing agents, such as hair washing shampoos, are based on tensides, that is on surface active agents, which usually are anion-active, non-ionic or amphoteric. Typical anion-active agents are long chained alkyl or alkyl aryl sulfate and sulfonate salts, such as alkali metal, typically sodium salts, or organic salts, such as di- and/or triethanolamine salts. Non-ionic surface active agents for use in cleansing compositions are, for example, ethoxylated fatty acid alkylamides and -esters.

From the patent literature a number of publications are known which relate to the use of different combinations of surface active agents in various cleansing compositions. As an example, EP patent application 232 153 may be mentioned, which relates to a detergent especially for washing dishes by hand, which besides an anionic detergent contains anionic alkyl ether sulfate (ethoxylated alkyl sulfate), foam improving agent, and in addition non-ionic, e.g. polyethoxylated alcohol or alkanolamide.

A shampoo intended e.g. for washing hair must not remove fat too effectively and it has to improve the shapeability of the hair. Shampoos for use in washing hair cannot be used as technical shampoos, for example for washing cars, due to their tendency to hydrolysis, which leads to a metal and paint corroding effect. In car shampoos, the triethanolamine salt of alkyl benzene sulfonates is used as the surface active ingredient, which does not corrode metal and does not leave stains on the paint surface. Such agents are, however, associated with negative health effects, which prevent their use, for example, for washing hair or as bath foam.

The foam stability of a bath foam has to good also at small concentrations, and it should facilitate the absorption of biologically beneficial substances through the skin.

Certain special properties are required also of shampoos intended for the treatment of rugs and hides.

The different tensides forming the base of the various shampoos also have to be compatible with the remaining components of the formula and ensure the homogeneity and clarity of the shampoo also under extended storage.

The manufacturing methods of the known shampoos are multi-stage erratic processes, labour intensive and thus economically unfavourable, and they do not lead to products with optimal quality properties.

Thus there is a need for such a basic tenside mixture which easy and economical to manufacture in pure form from easily available starting materials, and from which, by suitably adding adjuvants and additional tensides, products suitable for various applications are obtained.

Thus the object of the present invention is a process for the preparation of a cleansing composition which can be used in different technical and domestic fields, including personal hygiene, and which have improved quality properties.

The process according to the invention is characterized in that a mixture, which contains
 an alkali metal salt of an alkyl sulfonic acid, and optionally
 an alkali metal salt of an ethoxylated alkyl sulfate, is treated with concentrated, over 70% sulfuric acid in an amount excessive of the amount needed for liberating the organic acids, while stirring and simultaneously cooling, if necessary, so that the temperature of the mixture rises to at the most 35° C.,
the reaction mixture is allowed to separate into two layers,
the layer containing the organic acids is separated and neutralised with di- and/or triethanolamine to produce the di- and/or triethanolamine salts of the said acids, and optionally water and conventional additional agents and adjuvants are added.

As the alkyl sulfonate forming the main component of the method according to the invention, advantageously an alkali metal salt of an acid of the formula

is used, preferably a sodium salt, in which formula R means a primary or secondary alkyl group with 6 to 18 carbon atoms, or a mixture of alkyl groups. In the secondary alkyl group, the secondary carbon atom is attached to the sulfur atom (i.e. of the type R'R"CH-, where R' and R" are alkyl groups).

Such substances are commercially available, or they may be manufactured by known methods. A substance or mixture of substances suitable for the purpose is the sodium salt of $C_{10}$–$C_{18}$-alkyl sulfonic acid sold under the trade name "Volgonat", having a alkyl sulfonate concentration of appr. 60 to 80%, and which in addition contains small amounts of unsulfonated compounds and inorganic salts (sodium chloride, -sulfite and -sulfate a few percent, manufacturer and supplier Volzhski Chemistry Kombinat, Volgograd).

As the ethoxylated alkyl sulfate salt optionally present in the starting mixture, preferably an alkali metal salt of a compound having the formula

is used, especially the sodium salt, in which formula R has the meaning given above, and x means the integer appr. 2 to 6, usually 2 to 5.

These are commercially available substances, as an example the product sold under the name "sulfoetoxylat", manufactured by P/O Sintez, Nizhni-Novgorod.

By means of the method according to the invention, a basic tenside mixture is obtained, which as the anion active agent contains di- and/or triethanolamine salts of alkyl sulfonic acid and optionally of ethoxylated alkyl sulfate. From this basic mixture, cleansing compositions suitable for different purposes are obtained by suitably adding other tensides and/or adjuvants as well as water.

According to an advantageous embodiment of the method according to the invention, the incorporation of the said further tensides and adjuvants may be integrated with the preparation of the di- and/or triethanolamine salts itself. As further tensides, especially ethoxylated alkanolamides come into question as a non-ionic tenside, especially those having the formula $RCONHC_2H_4(OCH_2CH_2)_xOH$, where R has the meaning given above, and x is appr. 2 to 6, preferably 5 to 6. These are commercially available products. For example a product where x is 5 to 6 and R is a hydrocarbon chain of 10 to 16 carbon atoms, is commercially available under the name syntamide-5 (manuf. P/O Sintez, Nishni-Novgorod).

To the starting mixture of the method according to the invention advantageously also a mono- or dialkanolamide of the formula $RC(=O)$—$NR_1R_2$ may be added, wherein R has the meaning given above, and $R_1$ is hydrogen or hydroxy-$C_1$–$C_3$-alkyl, and $R_2$ is hydroxy-$C_1$–$C_3$-alkyl-Hydroxy-$C_1$–$C_3$-alkyl is advantageously hydroxyethyl.

The purpose of this component is to act i.a. as a foam stabilizer and thickener. These are available as commercial products, such as as mixtures containing alkyl groups of various length; as examples coconut or ricinic mono- or dialkanol-, such as -ethanolamides, and other mixed products may be mentioned.

Thus according to the invention, a mixture of alkali salts of alkyl sulfonate and optionally alkyl sulfate and, according to an advantageous embodiment, of the afore mentioned amides in water is treated with concentrated sulfuric acid of a concentration of more than appr. 70%, such as 75 to 92% (by weight). The amount of water with respect to the alkylsulfonate component is not very critical, but suitably appr. 1:1. The amount of starting materials and water as well as the concentration and amount of sulfuric acid are naturally interdependent as well as dependant on the desired end product and are chosen so as to remove the alkali metal from the starting materials and a free organic acid is formed. The excess of sulfuric acid is not critical, a suitable excess being for example appr. 30 to 35% of sulfuric acid of the said strength.

In accordance with the invention it is essential that the temperature of the reaction mixture does not rise, not even locally, above appr. 35° C. during the treatment. In order to even out the temperature, the mixture has to be stirred. Also the rate of addition of sulfuric acid may be used for controlling the temperature- If necessary, additional cooling may be employed, for example using external cooling with water.

After the addition, the mixture can still be stirred, suitably for appr. ½ to 1 hour, whereafter the mixture is allowed to set. Thus the mixture is separated into two layers, that is a lower layer containing relatively strong (over appr. 50%) residual acid and alkali metal sulfate, and an upper layer containing organic acids. The layers are separated and the upper layer is neutralised with di- and/or triethanolamine for the preparation of the di- and triethanolanine salts of the organic acids. When using diethanolamine, the mixture is lighter. Instead of this, technical grade triethanolamine may be used, which is a mixture of di- and triethanolamines. Good results have been obtained by using a vacuum distillate of technical grade triethanolanine. After the addition of the optional further ingredients and adjuvants, such as perfumes, cooking salt, preservatives etc., the shampoo is ready for use. Water is added to adjust the viscosity and to adjust the concentration of anion-active agents to a suitable level, which usually is 10 to 35% by weight.

The lower layer containing residual acid can, if desired, be treated with a base, such as potassium hydroxide, ammonia, mono-, di- or triethanolamine, whereby a product suitable as a fertilizer is obtained.

For the preparation of products having a suitable composition, the weight ratio of the anionic tenside components, i.e. the alkali metal salts of alkyl sulfonate and ethoxylated alkyl sulfate (100% active agent) to the sum of the amide components is suitably in the range of appr. 1:1 to 7:1, preferably appr. 2:1 to 4:1. The weight ratio of the alkyl sulfonate to alkyl sulfate, when the latter is used, is suitably at least appr. 3:2, preferably at least 2:1.

The weight ratio of the ethoxylated alkanolamide to the N-mono- and/or N,N-dialkanolamide is suitably appr. 1:1 to 6:1, a value suitable for many purposes being appr. 3:1 to 5:1, especially appr. 4:1.

According to a suitable embodiment, in the starting mixture 30–60 parts by weight of sodium alkyl sulfonate with an active agent concentration of 60 to 80%, 20 to 45 parts by weight of water, 5 to 12 parts by weight of thoxylated alkanolamide, 2 to 3 parts by weight of mono- or dialkanolamide, as well as at the most 15, usually at the most 10 parts by weight of sodium sulfoethoxylate is used. Such a mixture is treated for example with 25 to 70 parts by weight of a 75 to 92% strong sulfuric acid After separation of the layers, the upper layer containing the organic acids is neutralised with a sufficient amount of di- and/or triethanolamine.

According to an especially favourable embodiment, one starts from a mixture containing sodium alkyl sulfonate appr. 40 parts by weight (active agent concentration 60 to 80%) ethoxylated alkanolamide appr. 8 parts by weight, mono- or dialkanolamide appr. 2 parts by weight and sodium sulfoethoxylate appr. 2 parts by weight, as well as water appr. 20 to 35 parts by weight, which mixture is treated with appr. 40 parts by weight of a 75 to 92% strong sulfuric acid. After separation of the layers and neutralisation with triethanolamine, 100 parts by weight of a detergent composition is obtained, to which water and/or further additional ingredients may be added, if desired By means of the method according to the invention a product of an especially suitable composition may be prepared, i.e. a product which contains 30 to 50 parts by weight of a di-and/or a triethanolamine salt of alkylsulfonate, 5 to 10 parts by weight of ethoxylated alkanolamide, 2 to 5 parts by weight of mono- and/or dialkanolmide and 0 to 10 parts by weight of di- and/or triethanolamine salt of ethoxylated alkylsulfate, by using in the process corresponding alkali metal salts and amides in amounts necessary to give the said end product.

The method according to the invention makes it possible to prepare such an all-purpose shampoo which due to its multieffective surface active ingredients, which by means of the treatment according to the invention has been carefully purified from resins and other impurities, has soft detergent properties and an excellent skin care effect. The shampoo forms a strong and stable foam both in soft and hard water.

The shampoo prepared according to the invention is suitable for multipurpose use, e.g. as a hair or body shampoo, bath foam, a gentle textile detergent, also for washing domestic animals and as a car shampoo. For each individual application, to the product obtained as described above, additional ingredients known as such and suitable for the purpose may be added, such as dyes, perfumes, preservatives, cooking salt (viscosity regulation), biologically active agents, etc.

The basic shampoo obtained by the method is a homogenous, transparent liquid with a pleasant smell, without the smell of raw materials. Its pH may be adjusted in the neutralisation stage by means of the amount of base added, the pH being suitably in the range of appr. 5.0 to 8.5, the lower pH being suitable for dry and the higher for greasy hair.

The following examples illustrate the invention without limiting the same. The percentages are by weight unless otherwise indicated.

EXAMPLE 1

Into a round-bottomed, three-necked glass flask provided with a stirrer and a thermometer 400 g of alkyl sulfonate sodium salt (volgonat) is introduced having an active agent concentration of 60 to 70%, 200 g of water and the mixture is stirred for ½ hours. Into the aqueous solution of the alkyl sulfonate 80 g of ethoxylated amide (syntamide-5) and 20 g of monoalkanolamide ($C_{10}$–$C_{18}$ ethanolamide) are added. To the mixture, 250 g of 80% sulfuric acid is slowly added dropwise. During the dropwise addition of sulfuric acid, the container is cooled externally with cold water so that the temperature of the container does not exceed 35° C. When the sulfuric acid has been added, the stirrer is turned off and the contents transferred to a separating funnel and left to clarify for half an hour. Residual sulfuric acid having a strength of 53 to 58% is separated. The upper layer of organic substances is transferred to a round-bottom glass container and neutralised with triethanolamine, of which 350 g are needed. A ready product is obtained in an amount of 1000 g. To the product, 2.5 g of fir oil and 3.5 g of lavender extract are added.

EXAMPLE 2

Into a steel enamelled reaction container provided with a stirrer and having a volume of 2 m$^3$, 600 kg of alkyl sulfonate with an active agent concentration of 70% (Volgonat) is introduced, and 350 kg of water is added. After stirring the solution of surface active agent, 150 kg of sodium sulfoethoxylate is added which contains 2-3 oxyethylene groups in its alkyl chain, 120 kg of Syntamide-5 and 30 kg of alkyl ethanolamide ($C_{10}$–$C_{18}$ mixture). From an enamelled measuring flask 420 l of 92% strong sulfuric acid is added to the reaction mixture. Into the mantle of the container cold water is fed so that the reaction can be carried out at 25 to 35° C. After adding the acid, the stirrer is turned off and the reaction contents is allowed to clarify for one hour. After clarification, the lower layer is let into a reaction container containing triethanol amine and the residual acid of 55 to 56% strength is neutralised to an organic fertilizer. The mixture of organic acids remaining in the reaction container is neutralized with triethanolamine. 350 kg of triethanolamine is needed to obtain a neutral reaction (pH =7). 1500 kg of shampoo is obtained, viscosity 600 cSt. 2000 kg of a shampoo of 100 cSt is obtained.

EXAMPLE 3

600 g of sodium alkyl sulfonate of an active agent concentration of 60% (Volgonat) is introduced into a glass container provided with a stirrer and a thermometer and external cooling, and 300 g of water is introduced. To the mixture 120 g of Syntamide-5 and 25 g of diethanolamide ($C_{10}$–$C_{18}$ mixture) is added. After careful stirring 450 g of 75% sulfuric acid is slowly added to the mixture When all acid has been added, the contents are poured into a separating funnel and separated into two layers. The lower layer is neutralised with potassium hydroxide and forms a potassium fertilizer. The upper layer is neutralised with diethanolamine of which 250 g is consumed. A shampoo having a viscosity of 600 cSt is obtained in an amount of 1100 g. If the viscosity is adjusted to 80 to 100 cSt, 1600 to 1700 g of shampoo is obtained. In this case 1% of NaCl is added.

EXAMPLE 4

600 kg of sodium alkyl sulfonate (Volgonat, active agent concentration 60% , contains appr. 1% unsulfonated compounds and appr. 6% inorganic salts, sodium chloride, -sulfite and -sulfate) is added to a reactor together with 600 kg of water while stirring. Into the mixture is thereafter fed 450 l of sulfuric acid (76% strong, corresponds to appr. 756 kg) in small portions so that the temperature does not exceed 30° C. After the addition of the acid, the stirrer is turned off whereby the mixture separates into two layers within half an hour. A lower layer containing used sulfuric acid and an upper layer containing organic acids are obtained- The separation into layers takes place efficiently when the concentration of used sulfuric acid is 54 to 60% . The concentration can be monitored by measuring the density. The lower layer is separated and neutralised with a 20% KOH-solution. Instead of KOH, triethanolamine can be used for the neutralisation. The salt solutions obtained can be used in fertilizers, whereby a closed process without waste products is obtained.

The upper layer containing sulfonic acids is neutralised with triethanolamine (363 kg) to a pH of 6.0 to 8, whereby 1063 kg of ready tenside mixture is obtained which contains 64% of triethanolamine salts of alkylsulfonic acids. To this mixture, water and other tensides and adjuvants may be added if desired according to intended use.

I claim:

1. Process for the preparation of a tenside mixture, wherein a starting mixture containing
   an alkali metal salt of an alkyl sulfonic acid is treated with a concentrated sulfuric acid solution in an amount in excess of the amount needed for converting the salts to organic acids with stirring and cooling such that the temperature of the mixture does not exceed about 35° C.
   the reaction mixture being allowed to separate into two layers, one layer containing the organic acids,
   wherein the one layer containing the organic acids is separated and neutralized with di- or triethanolamine in order to prepare di- or triethanolamine salts of the said acids; wherein the starting mixture includes an ethoxylated alkanolamide, an N-mono- or N,N-dialkanolamide as a non-ionic tenside.

2. Process according to claim 1 wherein the starting material includes an alkali metal salt of an ethoxylated alkyl sulfate, the ratio of the alkyl sulfonate and alkyl sulfate components to the amide components being approximately 1:1 to 7:1.

3. Process according to claim 2 wherein the ratio of the alkyl sulfonate component to the alkyl sulfate component is at least about 3:2.

4. Process according to claim 2 wherein the ratio of ethoxylated alkonalamide to mono- and dialkylamide is approximately 1:1 to 6:1.

5. Process for the preparation of a tenside mixture, wherein a starting mixture containing
   an alkali metal salt of an alkyl sulfonic acid is treated with a concentrated sulfuric acid solution in an amount in excess of the amount needed for converting the salts to organic acids with stirring and cooling such that the temperature of the mixture does not exceed about 35° C.
   the reaction mixture being allowed to separate into two layers, one layer containing the organic acids.
   wherein the one layer containing the organic acids is separated and neutralized with di- or triethanolamine in order to prepare di- or triethanolamine salts of the said acids;
   wherein the alkalimetal salt of the alkyl sulfonic acid is a salt of an acid having the formula $RSO_3H$ in which R is a primary or secondary alkyl group with 6 to 18 carbon atoms or a mixture of alkyl groups.

6. Process according to claim 1 wherein the ethoxylated alkanolamide has the formula $RCONHC_2H_4(OCH_2CH_2)_xOH,$ wherein R is a primary or secondary alkyl group with 6 to 8 carbon atoms or a mixture of alkyl groups and x is an integer from 2 to 6.

7. Process according to claim 1 wherein the N-mono- and N,N.-dialkanolamide have the formula

RC(=O)—NR$_1$R$_2$ wherein R is a primary or secondary alkyl group with 6 to 18 carbon atoms or a mixture of alkyl groups and R$_1$ is hydrogen or hydroxy-C$_1$–C$_3$-alkyl, and R$_2$ is hydroxy-C$_1$–C$_3$-alkyl.

8. Process for the preparation of a tenside mixture, wherein a starting mixture containing an alkali metal salt of an alkyl sulfonic acid is treated with a concentrated sulfuric acid solution in an amount in excess of the amount needed for converting the salts to organic acids with stirring and cooling such that the temperature of the mixture does not exceed about 35° C., the reaction mixture being allowed to separate into two layers, one layer containing the organic acids, wherein the one layer containing the organic acids is separated and neutralized with di- or triethanolamine in order to prepare di- or triethanolamine salts of the said acids;

wherein the starting material includes an ethoxylated alkyl sulfate, the ethoxylated alkyl sulfate having the formula R(OCH$_2$CH$_2$)$_x$OSO$_3$H wherein R is a primary or secondary alkyl group with 6 to 18 carbon atoms or a mixture of alkyl groups and X is an integer from 2 to 6.

9. Process for the preparation of a tenside mixture, wherein a starting mixture containing an alkali metal salt of an alkyl sulfonic acid is treated with a concentrated sulfuric acid solution in an amount in excess of the amount needed for converting the salts to organic acids with stirring and cooling such that the temperature of the mixture does not exceed about 35° C., the reaction mixture being allowed to separate into two layers, one layer containing the organic acids, wherein the one layer containing the organic acids is separated and neutralized with di- or triethanolamine in order to prepare di- or triethanolamine salts of the said acids;

wherein the starting material contains:
1) 30 to 50 parts by weight of a di- or a triethanolamine salt of a compound having the formula RSO$_3$H,
2) 5 to 10 parts by weight of a compound of the formula RCONHC$_2$H$_4$(OCH$_2$CH$_2$)$_x$OH,
3) 2 to 5 parts by weight of an amide of the formula RC(=O)—NR$_1$R$_2$,
4) 0 to 10 parts by weight of a di- or triethanolamine salt of the compound R(OCH$_2$CH$_2$)$_x$OSO$_3$H wherein R is a primary or secondary alkyl group with 6 to 18 carbon atoms or mixture of alkyl groups, x is an integer from 2 to 6, R$_1$ is hydrogen or hydroxy-C$_1$–C$_3$-alkyl and R$_2$ is hydroxy-C$_1$–C$_3$-alkyl, further comprising adding water to the mixture in an amount selected to adjust the tenside mixture to a predetermined anionic activity and viscosity.

10. Process for the preparation of a tenside mixture, wherein a starting mixture containing an alkali metal salt of an alkyl sulfonic acid is treated with a concentrated sulfuric acid solution in an amount in excess of the amount needed for converting the salts to organic acids with stirring and cooling such that the temperature of the mixture does not exceed about 35° C.

the reaction mixture being allowed to separate into two layers, one layer containing the organic acids.

wherein the one layer containing the organic acids is separated and neutralized with di - or triethanolamine in order to prepare di- or triethanolamine salts of the said acids; wherein the starting material includes an alkali metal salt of an ethoxylated alkyl sulfate.

11. Process according to claim 10 wherein the alkali metal salt of the ethoxylated alkyl sulfate has the formula;

R(OCH$_2$CH$_2$)$_x$OSO$_3$Y wherein R is a primary or secondary alkyl group with 6 to 18 carbon atoms or a mixture of alkyl groups, x is an integer from 2 to 6 and Y is alkali metal ion.

* * * * *